United States Patent [19]

Khanna et al.

[11] Patent Number: 5,037,735
[45] Date of Patent: Aug. 6, 1991

[54] VISUAL DISCRIMINATION QUALITATIVE ENZYME COMPLEMENTATION ASSAY

[75] Inventors: Pyare L. Khanna, Fremont; Glenda L. Choate, Concord, both of Calif.

[73] Assignee: Microgenics Corporation, Concord, Calif.

[21] Appl. No.: 210,825

[22] Filed: Jun. 24, 1988

[51] Int. Cl.$^5$ ............... G01N 33/535; G01N 33/537; G01N 33/558

[52] U.S. Cl. ........................... 435/7.6; 435/7.9; 435/18; 436/500; 436/501; 436/514; 436/538

[58] Field of Search ............... 435/7, 810, 14, 11, 435/18, 184, 174, 180, 7.6, 7.8, 7.9; 436/500, 501, 514, 538

[56] References Cited

U.S. PATENT DOCUMENTS

| | | |
|---|---|---|
| 4,708,929 | 11/1987 | Henderson . |
| 4,756,828 | 7/1988 | Litman et al. . |
| 4,786,591 | 11/1988 | Draeger et al. . |
| 4,818,677 | 4/1989 | Hay-Kaufman et al. . |
| 4,937,188 | 6/1990 | Giese et al. ........................... 435/7 |

OTHER PUBLICATIONS

Dimitriadis, G. J., "Effect of Detergents on Antibody-Antigen Interaction", in *Analytical Biochemistry* (1979), 98:445–451.

*Primary Examiner*—David Saunders
*Attorney, Agent, or Firm*—Richard L. Neeley

[57] ABSTRACT

A β-galactosidase complementation assay for determining the presence of an analyte which is a member of a specific binding pair (sbp) in a sample is provided, which assay permits visual discrimination between those samples wherein the analyte is present above a predetermined, threshold concentration. The method comprises combining the sample with a hydrophobic enzyme donor- (ED-) analyte conjugate and the complementary member of the sbp to form an sbp complex-containing assay medium. A small volume of the assay medium is spotted onto an enzyme acceptor (EA) affixed to a bibulous, solid support, followed by development with enzyme substrate solution. A substantially larger area is detectable when analyte in the sample is below as compared to above a threshold concentration. The assay is particularly useful in field testing applications such as determining the presence of antibiotics in milk, toxins in water, or drugs in serum or urine. Kits facilitating the method are also provided.

17 Claims, No Drawings

5,037,735

VISUAL DISCRIMINATION QUALITATIVE ENZYME COMPLEMENTATION ASSAY

TECHNICAL FIELD

The present invention relates to enzyme immunoassays and, in particular, to β-galactosidase complementation assays.

BACKGROUND OF THE INVENTION

Immunoassays have been developed based on a number of different methodologies for detecting a wide variety of analytes. Most of the assay methods require a skilled technician and laboratory equipment. Although there is a need for assays which can be performed in the field, only a few assays have been successfully adapted. For example, an enzyme-linked immunosorbent assay (ELISA) for determining levels of hormone indicative of pregnancy has been marketed for home use. However there is a need for an assay for field use for other types of applications such as for testing urine for controlled substances, water for pollutants, or milk for antibiotics. In addition to being fast and easy to perform and requiring little or no equipment to prepare and analyze, the assays must be sensitive and accurate.

RELEVANT LITERATURE

Modified β-galactosidase enzyme donors and enzyme acceptors have been prepared by chemical synthesis and recombinant engineering. The modified fragments retain β-galactosidase activity upon complementation and facilitate production of and attachment of analyte to the fragments. See for example U.S. Pat. No. 4,708,929 and the articles cited therein.

SUMMARY OF THE INVENTION

A β-galactosidase complementation assay for determining the presence of an analyte which is a member of a specific binding pair (sbp) in a sample is provided, which assay permits visual discrimination between those samples wherein the analyte is present above a predetermined, threshold concentration. The method comprises combining the sample with a hydrophobic enzyme donor- (ED-) analyte conjugate and the complementary member of the sbp to form an sbp complex-containing assay medium. A small volume of the assay medium is spotted onto an enzyme acceptor (EA) affixed to a bibulous, solid support, followed by development with enzyme substrate solution. A substantially larger area is detectable when analyte in the sample is below as compared to above a threshold concentration. The assay is particularly useful in field testing applications such as determining the presence of antibiotics in milk, toxins in water, or drugs in serum or urine. Kits facilitating the method are also provided.

DESCRIPTION OF THE SPECIFIC EMBODIMENTS

A β-galactosidase complementation assay method for detecting the presence of a threshold concentration of an analyte is provided, which analyte is a member of a specific binding pair (sbp). The method utilizes a β-galactosidase enzyme acceptor (EA) affixed to a bibulous, solid support to form EA paper. The sample is combined with a hydrophobic enzyme donor- (ED-) analyte conjugate and the complementary member of the specific binding pair for a sufficient time for the complementary member to react competitively with conjugate and any analyte present in the sample to form an assay medium containing a complex between the sbp members. A small volume of the assay medium is spotted onto the EA paper and wicks radially from the application site. The EA paper is then combined with an enzyme substrate solution. A substantially larger area is detectable when the analyte is below a threshold concentration as compared to above the concentration.

The assay method can be used to detect any analyte determined by prior art immunoassay or complementation methods. The assay method can be used with any aqueous medium containing the analyte. The analyte may be an immunogen, e.g. a peptide, protein or carbohydrate having a high molecular weight (MW>1000), but usually will be a hapten (MW<1000) such as a drug or toxin. The method is particularly suitable for analytes that are desirably tested in the field such as for a detection of a controlled substance which may be present in a bodily fluid such as urine, serum or plasma. The method also finds use to detect antibiotics in milk or toxins such as pesticides, dioxin, parathion or the like in water or soil samples. Other than providing the sample in an aqueous solution and removing particulates, no pretreatment of the sample will usually be performed for purposes of the instant assay method.

The enzyme donor and enzyme acceptor are partial sequences of β-galactosidase. Either partial sequence may be mutated to facilitate production of the sequence, attachment of an analyte or the like. The enzyme acceptor and enzyme donor-analyte conjugate are characterized by forming an active enzyme complex when brought together. When the enzyme donor-analyte conjugate is bound to the complementary specific binding pair member, the observed enzyme activity is different from that observed in the absence of the complementary member of the specific binding pair. Thus, the availability of complementary member of the specific binding pair to bind with enzyme donor-analyte conjugate will vary with the amount of analyte in the medium.

β-Galactosidase enzyme donors and acceptors are described in U.S. Pat. No. 4,708,929, which disclosure is incorporated herein by reference, as are analytes and enzyme donor-analyte conjugates. Copending U.S. patent application Ser. No. 151,412 filed Feb. 2, 1988, describes reaction conditions and reagents for complementation assays. The conditions of the assay described in that application are applicable to the subject invention.

A β-galactosidase EA will be affixed to a bibulous, solid support to form EA paper. The support may be any bibulous material that binds EA sufficiently tightly so that the EA will affixed to the support when the support is immersed in an aqueous solution, which binding does not interfere with complementation. Additionally, the support will provide a sufficiently hydrophobic environment so that a hydrophobic ED-analyte conjugate applied to the support will not migrate from the application site or will migrate only a small distance. Numerous bibulous solid supports used in immunoassay wicking methods are reported in the literature which include modified cellulosic supports such as paper, nitrocellulose and desirably, noncellulosic supports such as nylon membranes, polyester-based membranes and polyamide-based membranes. Conveniently, the solid support will be a chemically-reactive membrane, such as a treated nylon membrane, that covalently or non-covalently binds proteins incubated with the membrane. Nylon membranes reported to covalently bind proteins, apparently through formation of a bond with protein amino groups, are commercially available from sources including Millipore Corporation ("Immobilon") and Pall Corporation ("Immunodyne"). Immunodyne membranes are preferred as membrane-affixed EA was stable for longer periods upon storage with Immunodyne membranes than with Immobilon membranes.

The enzyme acceptor will be bound to the solid support by conventional means for covalently or non-covalently attaching a protein to the support material. A preferred method for attaching EA to Immobilon membranes is described in detail in the Experimental section. Usually, the enzyme acceptor will cover the entire surface of the solid support. However, EA may be applied to selected portions of the paper. Desirably, the EA will be on the surface of the paper at a substantially uniform concentration. After attachment of the enzyme acceptor, the paper will be carefully washed, desirably with an aqueous buffer solution containing a surfactant, to remove EA which is not tightly bound to the paper. After attachment of EA, the paper may be covered with a blocking agent such as bovine serum albumin (BSA) or casein to minimize non-specific binding of proteinaceous substances to the EA paper. Following preparation, the EA paper is blotted dry and stored, desirably in a vacuum desiccator. Storing the paper under dry conditions has been found to enhance the stability of the EA. The paper can be stored at room temperature or refrigerated for longer stability.

An ED-analyte conjugate is used which is sufficiently hydrophobic to remain in the area in which it is applied to EA paper in the absence of binding to its complementary specific binding pair member. However, when the conjugate is combined with the complementary member of the specific binding pair, the conjugate will migrate radially a substantially greater distance from the application site, which distance will define a substantially larger detectable area following exposure to enzyme substrate. Desirably, the conjugate will wick radially from the application site at least twice as far, usually four times as far, preferably to the solvent front, when complexed with its specific binding pair member.

The analyte or analyte analogue joined to the ED may produce a sufficiently hydrophobic conjugate to provide for discrimination between positive and negative assay results. If not, one or more hydrophobic substituents can be joined to the ED to provide a hydrophobic conjugate. Desirably, hydrophobic atoms such as C, H, S or halogens will comprise at least about 50%, usually at least about 60% by weight of the total substituents, including the analyte, on the ED. Any additional substituent(s) may be joined to the ED at the same or a different site from the analyte attachment site. When joined at the same site as the analyte, the substituent may be bound only to the analyte or may serve as a linking group, desirably of at least about 6 carbon atoms, joining the analyte to the ED. The substituent(s) may be one or more hydrophobic moieties such as cholesterol, a fatty acid, T3 or T4.

Exemplary functional methods for determining whether the conjugate is sufficiently hydrophobic to discriminate between positive and negative samples are described in detail in the Experimental section. Those methods are based on determining the difference in distance the conjugate migrates when spotted on the EA paper following preincubation in an assay medium with and without the complementary specific binding pair member.

Numerous specific binding pairs which may find use in immunoassays are known. Either member of the pair may serve as the analyte, so long as binding of the complementary member to the conjugate provides for a difference in the ability of the conjugate to complement on the surface of the EA paper. Usually, at least one member of the specific binding pair will be a protein or a protein fragment, e.g. antigen/antibody, lectin/sugar, etc. Usually the pair will be a receptor/ligand pair in which the ligand serves as the analyte. As the receptor, an antibody will usually be employed, either polyclonal or monoclonal. Alternatively, other receptor/ligand pairs may be used, e.g., vitamin B12-intrinsic factor and folic acid-folate binding protein.

After combining with sample to form an assay medium, the concentration of enzyme donor-analyte conjugates will usually be in the range of about 1 nM to about 60 nM, more usually about 1 nM to about 10 nM. The enzyme acceptor will usually be present on the EA paper in substantial excess. The molar ratios of enzyme donor-analyte conjugate to enzyme acceptor will usually be 1:50 to 1:10,000, usually 1:100 to 1:2000. The concentration of the enzyme donor-analyte conjugate and complementary specific binding pair member provides ED-analyte conjugate that is not bound to analyte receptor when a predetermined, threshold concentration of the analyte is present in the sample.

The optimal ratio of ED-analyte conjugate and its complementary specific binding pair member will be determined in the presence of EA so as to detect a predetermined threshold concentration of analyte and also to minimize the background activity. The response in relation to background level is optimized. One of the possible methods to optimize the concentrations, conveniently, is a two step procedure. First, the ratio of the concentration of ED-analyte conjugate and complementary specific binding pair member will be such as to substantially achieve minimum enzyme rate under assay conditions, while maintaining linearity of the rate varying with analyte concentration in the desired analyte concentration range. This concentration is desirably determined in solution by studying the kinetics of the reaction. See, for example, copending application Ser. No. 151,412 filed Feb. 2, 1988, which describes in detail optimizing conjugate and antibody concentrations. Usually, the concentrations of complementary specific binding pair member and conjugate will be within at least 85%, more usually within at least 95% of the concentration necessary to optimize conditions. Additionally, when the complementary specific binding pair member is an antibody, adding a second antibody specific for the anti-analyte antibody prior to contact with the EA paper may lower the $\beta$-galactosidase-catalyzed reaction rate.

After the optimal complementary specific binding pair member and conjugate concentrations in the desired analyte concentration range are determined in a solution assay, those concentrations are used in a wicking assay. Varying amounts of complementary specific binding pair member are added until the conjugate remains in the application site area when using a sample having just above the threshold analyte concentration. Migration of the conjugate from the application site is observed with a sample having the threshold concentration or less analyte. The minimum complementary specific binding pair member concentration which provides for conjugate migration at threshold analyte concentration is optimal for use in the assay.

The assay conditions and the buffer in which the sample, ED-analyte conjugate and analyte receptor are combined provide for formation of a complex between the complementary specific binding pair member and ED-analyte conjugate or analyte in an assay medium. As the assay medium is spotted on the EA paper, the buffer also provides for complementation between enzyme donor and enzyme acceptor to form solid support-affixed $\beta$-galactosidase. The buffer formulation is not critical. In general, physiological buffers such as phosphate buffered saline, tris buffer and like buffers are useful. A preferred buffer comprises about 100 mM to about 300 mM $NaPO_4$, about 5 mM to about 10 mM EGTA, and about 10 mM to 20 mM $NaN_3$ having a pH of between 6 and 8. The temperature will usually be at least about 20° C., preferably elevated, but below 60° C. As the assay is designed to be used in the field, most assays are performed at about 20° C. to about 30° C., more usually about 25° C. The assays are performed at atmospheric pressure.

As a first step for detecting the presence of analyte in a sample, the sample is incubated with the ED-analyte conjugate and complementary specific binding pair member to form a specific binding pair complex for a time sufficient for the complementary specific binding pair member to react with analyte. The time will vary depending on the incubation temperature and the affinity of the specific binding pair members and will usually be sufficient for the reaction to reach equilibrium. Usually the incubation is at about 20° C. to about 37° C. for at least about 15 min., more usually for about 30 to 60 min. Conveniently, the ED-analyte conjugate and complementary specific binding pair member are combined to form a specific binding pair complex prior to contact with sample. The complex will be incubated with the sample for a time sufficient for analyte in the sample to react with the complementary specific binding pair member in the complex prior to spotting onto the EA paper. When using a preformed complex, equilibrium was reached in 15 to about 60 min. following addition of the complex to the sample in an exemplary digoxin assay using polyclonal antibodies.

When mixed with ED-analyte conjugate and the complementary specific binding pair member in a buffer to form an assay medium, varying amounts of the sample can be used, which amounts depend on the anticipated analyte concentration in the sample. Usually the sample will comprise at least about 1-20% of the volume of the assay medium.

A small volume of the assay medium will be applied to the EA paper. The amount of the assay medium will be sufficiently small to be drawn out or wicked out of the application device by the dry EA paper and will not flood or bead up on the paper. Conveniently, not more than about 10 $\mu l$, usually about 3 to about 5 $\mu l$, will be used. The assay medium volume will conveniently be the volume to be applied to the EA paper or a somewhat larger volume which permits use of very small sample volumes and avoids wasting assay reagents. However, substantially larger assay medium volumes can be used when desired for convenience of measurement or the like.

The assay medium will be applied, conveniently by contacting a capillary tube containing the medium with a predetermined area of the EA paper, and will wick radially from the application site. The EA paper will be incubated for about 5 to about 30 min., more usually about 10 to 30 min., depending upon the temperature. Usually incubation will be for a time sufficient for EA to react with ED to form solid support-affixed $\beta$-galactosidase.

The EA paper is thereafter incubated with an enzyme substrate solution. An enzyme substrate is employed that when cleaved by the enzyme results in a change of the amount of light absorbance (optical density) or emission of the assay medium. That is, cleavage of the substrate results in the appearance or disappearance of a colored or fluorescent product. The enzyme substrate may produce a precipitating or non-precipitating product. Desirably when using a non-precipitating product, the product will be non-specifically bound to the EA paper. A preferred enzyme substrate is chlorophenol red galactoside (CPRG). CPRG and other comparable enzyme substrates such as ortho-nitrophenyl-$\beta$-D-galactoside (ONPG) are commercially available. Incubation with enzyme substrate is conveniently performed by immersing the EA paper in the enzyme substrate solution. When using CPRG, the EA paper will conveniently be incubated for from 1 to 10 min. at room temperature in a solution of between about 0.5 to 2 mM CPRG. EA may be added to the substrate solution to enhance color development, if desired. Alternatively, the substrate may be incorporated into the EA paper or be present in the assay medium, rather than as a separate solution. In that case, incubating the assay medium with the EA paper will provide for development of the EA paper.

When the sample contains an analyte concentration above the predetermined threshold concentration, the conjugate remains near the application site and produces a small detectable area after development with substrate. When using CPRG a small, dark dot is formed at the application site. When the analyte is not present at a concentration above the predetermined, threshold level, the conjugate wicks to a substantial distance from the application site to form a substantially larger detectable area with a much less dense color.

A kit containing reagents facilitating the present invention is also contemplated. The kit comprises EA affixed to a bibulous, solid support and a $\beta$-galactosidase ED-analyte conjugate and the complementary member of the specific binding pair. The ED-analyte conjugate and the complementary specific binding pair member may be provided in the same or different containers, conveniently, in the same container as a preformed complex. Enzyme substrate solution may be included in the kit or sold separately. The kit may additionally contain positive and negative analyte controls. The EA paper will be provided in dry form. The additional reagents may be provided in liquid or dry form. Conveniently, the additional reagents will be provided in a tablet containing a quantity of reagent sufficient for one assay.

The following examples are offered by way of illustration and not by way of limitation.

EXPERIMENTAL

EXAMPLE 1

Preparation of EA Paper

To bind EA to membranes, the membranes were shaken for 30 min. at room temperature (RT) covered in a solution of EA22 (at a concentration of about 5-10 $\mu M$ in 50 mM $PO_4^{3-}$ buffer pH 7.4). The membranes were then blocked with a solution of 1% casein in PBS (shaking, 60 min., RT), followed by two rinses in PBS containing 0.05% Tween 20 (shaking, 15 min., RT). The membranes were then blotted dry and stored in a vacuum desiccator.

For complete binding of proteins to occur, it is preferable that there are no thiols to compete for protein binding sites on the membrane. Thus, the EA used for the following examples was "exchanged" EA22 in which the storage thiols were removed by passage over a Sephadex column.

Exchanged EA was stored for up to 7 days refrigerated with or without the addition of EGTA for thiol protection or was frozen with 10% glycerol for storage of 7 or more days to provide for comparable enzyme activity following immobilization.

EXAMPLE 2

Optimization of Concentration of Antibody and ED-Analyte Conjugate

An immune complex was prepared first by incubating 50 nM ED4T3 in 250 mM $PO_4^{3-}$ buffer containing 1-8 mM EDTA and 6 mM $Mg(OAc)_2$ and 1:200 dilution of monoclonal anti-T3 antibody for 45 min. at 37° C. This immune complex was then diluted to 5 nM and compared with 5 nM ED4T3 using the radial wicking mode. The immune complex wicked to the solvent front as opposed to ED4T3 which remained in a small dot at the application site. Thus, there was excellent discrimination between the presence or absence of antibody.

The next experiment was a titration of the concentration of anti-T3 antibody in the immune complex to optimize the concentration used. An immune complex was made with anti-T3 antibody (1:1600 to 1:200 range) which was then spotted on Pall-EA paper. Immune complex wicked radially with the solvent front when either 1:200 or 1:400 dilutions of anti-T3 was used. However, when the 1:1600 dilution was used, a dark central dot began to appear following development with CPRG, indicating that conjugate was present which was not bound to antibody. Once conditions were established which demonstrated discrimination between the presence or the absence of antibody, the next study was an attempt to discriminate the presence of a threshold concentration of analyte.

A more concentrated immune complex was prepared for this study: 500 nM ED4T3 and 1:100 anti-T3 antibody. This complex was diluted to 2 nM ED4T3 and 1:25,000 anti-T3 and incubated with 50 ng/ml T3 calibrator at 37° C. for 15 min. The sample with analyte dose showed a distinct dark inner dot compared with the sample without analyte.

EXAMPLE 3

Antibody/Conjugate Ratio for Detecting A Predetermined Analyte Concentration

An assay wherein a certain predetermined threshold concentration of analyte is required to produce the dark, inner spot using CPRG and an analyte dose lower than that concentration would produce the lighter spot with a diameter equal to the solvent front was developed. The first study used an immune complex prepared with 50 nM ED4T3 and 1:400 anti-T3, which was then diluted 10-fold and incubated with 0, 10, 25, 50, or 90 ng/ml T3 (system concentration). Dark, inner dots were seen at all T3 doses. However, the color was lighter at the 50 and 90 ng/ml dose due to the inhibition of complementation by the high percentage of serum of the calibrator (as shown separately in a kinetic assay in solution). The difference in the rates in solution between the 0 and 10 ng/ml sample represented 42% vs 61% of the infinite analyte dose (90 ng/ml T3). Thus, a net difference of about 19% of the solution rates by the 10 ng/ml T3 sample was sufficient to allow discrimination of the inner spot in a wicking assay.

To make the assay respond to a higher threshold concentration of T3 (50 ng/ml), the concentration of anti-T3 was raised to 1:100 for the formation of the immune complex. No inner dot was seen with 50 ng/ml T3. The comparable rates when assayed in solution indicated that the 50 ng/ml dose had reached only 44% of the open rate, that is, the rate with infinite analyte dose. The closed rate, the rate with threshold analyte concentration, reached 34% of the open rate. Thus the difference between these two samples was only a net gain of 10%. The data from these two studies indicates that a net difference between about 10 to about 19% produced the inner dot in the assay, and thus discrimination between samples with concentrations above and below the threshold concentration.

A last study was performed with immune complex prepared in the presence of 1:200 anti-T3 antibody. The enzyme rate was monitored in solution and a volume of assay medium spotted radially as above. The rates show:

| Solution | | Wicking |
| --- | --- | --- |
| 0 T3 = 37% open rate | | no inner dot |
| 10 T3 | 39 | no inner dot |
| 20 T3 | 52 | + inner dot |
| 40 T3 | 63 | + inner dot |

Thus the 20 ng/ml sample, which was the minimum dose to yield the inner dot, was a result of a net increase of 15% over the closed rate. It is evident from these studies, that a threshold assay can indeed be developed for other analytes by titrating the antibody to achieve an immune complex which is sensitive to the desired analyte concentration.

EXAMPLE 4

Effect of Detergents

All conjugates used in the previous examples were prepared in 250 mM phosphate buffer without any stabilizers. Since conjugates are desirably stored with stabilizers, the effect of two detergents on the wicking of ED4 and ED4T3 was tested. Solutions of ED4 and ED4T3 (5 nM) were prepared with or without 0.24% Lauroylsarcosine or 0.9% Tween 20 and spotted on a Pall-EA membrane as previously. The detergents had no effect on the wicking or color development of ED4. The presence of Tween 20 caused only a slight increase in the radius of the ED4T3 sample. Although each specific conjugate and detergent combination will desirably be tested, this study indicates that the addition of detergents to an assay reagent will not interfere with the assay.

EXAMPLE 5

Hydrophobicity of Conjugates

Various concentrations of ED4T3 (1 to 100nM) were spotted and allowed to wick radially with Pall membranes which had not been incubated with EA but which had been blocked with 1% casein. The membranes were developed with EA and CPRG. In all cases, the color was restricted to a central dot, which did not reach the solvent front. Thus, the blocked-Pall membranes did not allow wicking of ED4T3 to the solvent front, although in previous studies ED4 wicked to the solvent front. This non-specific binding of conjugate was attributed to the hydrophobic nature of the ED-T3 conjugate and a series of other conjugates was studied to determine the degree of hydrophobicity required for discrimination between positive and negative samples.

EA paper, prepared by reacting Pall membranes with 5 μM EA, were spotted with 3 to 5 μl of 10 nM solutions of various conjugates. As in the earlier study, the ED4 spot extended to the solvent front, while ED4T3 remained as a small dot. ED4T4 behaved identically to ED4T3. ED4-Digoxin remained in the center, although the radius was larger than the T3 and T4 conjugate spots. ED4-B12 extended to the solvent front. Solutions of ED4-KLH and ED4-BSA, though poorly reactive, also extended to the solvent front.

These results demonstrate that the amount of conjugate migration in the absence of antibody correlates inversely with the hydrophobicity of the conjugate. That is, the T3 and T4 conjugates are the most hydrophobic, followed by the digoxin conjugate and these are the only conjugates which did not wick with the solvent front.

EXAMPLE 6

ED4-B12 Assay

The studies with ED4T3 were repeated with conjugates which are less hydrophobic than ED4T3. ED4-B12 was incubated with a range of concentrations of anti-B12 (1:5000 to 1:100) to form immune complexes. These were assayed in solution to determine inhibition of complementation and were spotted on Pall-EA paper. At the lowest anti-B12 concentration, the solution assay was inhibited only 22% and there was no decrease in color development with the membrane spot. A decrease in color development on the membrane was observed with the immune complexes formed with higher anti-B12 concentrations, which correlated with the increase in inhibition of complementation (55 to 64% inhibition with 1:1000 to 1:100 anti-B12) in solution assay. To "open up" this assay, the immune complex (1:2000 anti-B12) was incubated with 5 to 100 nM B12 before assay and spotting. The complex was inhibited 44% without dose and 34% with the highest B12 concentration indicating that the ratio of ED-B12 and anti-B12 needs optimization. However, the area of color development was affected only slightly by the presence of an analyte dose. The color density out to the solvent front was identical with the no analyte sample, while there was a slight increase in density in the very center. From this data, it is evident that an sensitive assay could be developed for B12 once the concentrations of the various components have been optimized.

EXAMPLE 7

ED4-Digoxin Assay

The wicking assay format was also tested using the Digoxin conjugate of ED4. Immune complex was formed with 34 nM ED4-Digoxin, 1:500 polyclonal anti-Digoxin, and 1:6 goat anti-rabbit serum (GARS). This complex was subsequently incubated 30 min. at 37° C. with analyte dose (0 or 100 ng/ml Digoxin), assayed in solution and also spotted on Pall-EA membranes for the wicking assay. The activity of the 100 ng/ml sample with antibody was 51% the rate of the sample without antibody. The 0 ng/ml sample rate was 34%, yielding a net 15% difference in 100 ng/ml sample in solution. The color development of the 0 ng/ml sample was much fainter than the 100 ng/ml sample. These results are similar to those of the T3 conjugate. That is, a net kinetic difference between about 10 and about 20% is sufficient to distinguish a sample having a threshold concentration of analyte from a less concentrated sample.

The study was repeated to optimize the distinction between the 0 ng/ml and 100 ng/ml samples. By increasing the immune complex formation time to 60 min., the net kinetic difference in solution between the samples was increased to 33%. However, there was no further enhancement of the distinction of membrane color development. By omitting the GARS, the color development of all the samples was increased and very good color distinction was obtained with the membranes.

As demonstrated by the above examples, the present invention provides a simple assay method which provides for visual discrimination between the presence and absence of analyte in a sample above a predetermined concentration. The assay procedure requires minimal manipulation and a small number of reagents, so that it can be readily performed in the field.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method for determining the presence of an analyte in a sample wherein said analyte is a member of a specific binding pair, said method comprising:
   (a) combining said sample with a solution comprising a hydrophobic β-galactosidase enzyme donor- (ED-) analyte conjugate and the complementary specific binding pair member for a time period sufficient for analyte conjugate and any analyte to react with said complementary specific binding pair member to form a specific binding pair complex-containing assay medium;
   (b) applying a volume of said assay medium sufficient for wicking from an applicator to a predetermined application site area of a bibulous solid support comprising a β-galactosidase enzyme acceptor (EA) affixed to said solid support and capable of forming with said (ED)-analyte conjugate an active enzyme complex having β-galactosidase activity;
   wherein said conjugate and said support are sufficiently hydrophobic so that said conjugate will remain substantially in the area applied;
   (c) incubating said solid support for a time sufficient to form solid support-affixed β-galactosidase; and (d) incubating said solid support with an enzyme substrate which forms a visually detectable product upon reaction with β-galactosidase;

whereby a substantially larger product area extending from said application site area is detectable when the concentration of said analyte is below a threshold concentration as compared to a detectable product area extending from said application site area when said analyte is above said threshold concentration.

2. The method of claim 1 wherein said enzyme substrate is present either in said assay medium or affixed to said solid support-affixed enzyme acceptor EA.

3. The method of claim 1 wherein said sample is a bodily fluid.

4. The method of claim 1 wherein said bibulous, solid support is a non-cellulosic membrane.

5. The method of claim 1 wherein said membrane is a nylon membrane.

6. The method of claim 1 wherein EA is present on said solid support at a uniform concentration.

7. A method for determining the presence of an analyte in a sample wherein said analyte is a member of a specific binding pair, said method comprising:
  (a) combining said sample with a solution comprising a hydrophobic β-galactosidase enzyme donor- (ED-) analyte conjugate and the complementary specific binding pair member for a time period sufficient for analyte conjugate and any analyte to react with said complementary specific binding pair member to form a specific binding pair complex-containing assay medium;
  (b) applying a volume of said assay medium sufficient for wicking from an applicator to a predetermined application site area of a bibulous solid support comprising a β-galactosidase enzyme acceptor (EA) affixed to said solid support and capable of forming with said (ED)-analyte conjugate an active enzyme complex having β-galactosidase activity;
  wherein said conjugate and said support are sufficiently hydrophobic for said conjugate to remain in substantially the area applied;
  (c) incubating said solid support for a time period sufficient to form solid support-affixed β-galactosidase; and
  (d) incubating said solid support with an enzyme substrate which forms a visually detectable product upon reaction with β-galactosidase
  whereby a substantially larger product area extending from said application site area is detectable when the concentration of said analyte is below a threshold concentration as compared to a detectable product area extending from said application site area when said analyte is above said threshold concentration.

8. The method of claim 7 wherein said analyte conjugate and said complementary specific binding pair member are present as a preformed complex when said sample is combined with said solution to form said assay medium.

9. The method of claim 7 wherein said specific binding pair is antigen/antibody.

10. The method of claim 9 wherein said antigen is said analyte.

11. The method of claim 7 wherein said analyte is hydrophobic.

12. The method of claim 11 wherein said analyte is hydrophilic and said ED-analyte conjugate additionally comprises at least one hydrophobic moiety.

13. The method of claim 12 wherein said hydrophobic moiety is cholesterol, a fatty acid, triiodothyronone (T3) or thyroxine (T4).

14. The method of claim 7 wherein said enzyme substrate produces a non-precipitating product.

15. The method of claim 14 wherein said enzyme substrate is chlorphenolred galactoside (CPRG).

16. A method for determining the presence of a drug in a serum or urine sample comprising:
  (a) combining said sample with a solution comprising a hydrophobic β-galactosidase ED-drug-conjugate and a receptor specific for said drug for a time sufficient for ED-drug-conjugate and any drug to react with said receptor to form an ED-drug-conjugate- and drug-receptor complex-containing assay medium;
  (b) applying a volume of said complex-containing assay medium to a predetermined application site area of a noncellulosic membrane comprising a membrane affixed β-galactosidase enzyme acceptor (EA);
  wherein said conjugate and said support are sufficiently hydrophobic for said conjugate to remain in substantially the area applied;
  (c) incubating for a period of time sufficient for EA to react with ED to form membrane-affixed β-galactosidase; and
  (d) combining said membrane affixed β-galactosidase with an enzyme substrate solution which forms a detectable colored product upon reaction with β-galactosidase;
  whereby a substantially larger colored product area extending from said application site area is detectable when the concentration of said drug is below a threshold concentration as compared to a detectable colored product area extending from said application site area when said drug is above said threshold concentration.

17. A method for determining the presence of T3 in a serum sample comprising:
  (a) incubating said sample with a solution comprising from about 1 to about 10 nM β-galactosidase ED-T3 conjugate and anti-T3 antibody for about 30 to about 60 min. at about 37° C. to form an immune complex-containing assay medium;
  (b) applying a small volume of said assay medium to β-galactosidase EA affixed at a uniform concentration to an application site area of a nylon membrane;
  (c) incubating for about 10 to about 30 min. at about 37° C. to form membrane-affixed β-galactosidase;
  (d) combining said membrane-affixed β-galactosidase with 0.5 to 2 mM CPRG solution to form a detectable colored reaction product whereby a substantially larger product area extending from said application site area is detectable when the concentration of T3 is below a threshold concentration as compared to a detectable product area extending from said application site area when T3 is above said threshold concentration.

* * * * *